US012781286B2

(12) United States Patent
Mcclain et al.

(10) Patent No.: US 12,781,286 B2
(45) Date of Patent: Nov. 3, 2026

(54) METHODS TO DETECT AND TREAT SARS-CoV-2 (COVID19) INFECTION

(71) Applicants: DUKE UNIVERSITY, Durham, NC (US); THE U.S. GOVERNMENT AS REPRESENTED BY THE DEPT. OF VETERANS AFFAIRS, NW Washington, DC (US)

(72) Inventors: Micah Mcclain, Durham, NC (US); Chris Woods, Durham, NC (US); Geoffrey Ginsburg, Durham, NC (US); Ephraim Tsalik, Cary, NC (US); Ricardo Henao Giraldo, Durham, NC (US); Thomas Burke, Durham, NC (US); Florica Constantine, Albany, CA (US); Elizabeth Petzold, Durham, NC (US)

(73) Assignees: DUKE UNIVERSITY, Durham, NC (US); THE U.S. GOVERNMENT AS REPRESENTED BY THE DEPT. OF VETERANS AFFAIRS, Washington, DC (US)

( * ) Notice: Subject to any disclaimer, the term of this patent is extended or adjusted under 35 U.S.C. 154(b) by 961 days.

(21) Appl. No.: 18/000,858

(22) PCT Filed: Jun. 11, 2021

(86) PCT No.: PCT/US2021/036961
§ 371 (c)(1),
(2) Date: Dec. 6, 2022

(87) PCT Pub. No.: WO2021/252864
PCT Pub. Date: Dec. 16, 2021

(65) Prior Publication Data

US 2023/0212699 A1 Jul. 6, 2023

Related U.S. Application Data

(60) Provisional application No. 63/045,881, filed on Jun. 30, 2020, provisional application No. 63/038,012, filed on Jun. 11, 2020.

(51) Int. Cl.
*C12Q 1/70* (2006.01)
*G16H 50/20* (2018.01)

(52) U.S. Cl.
CPC ............... *C12Q 1/70* (2013.01); *G16H 50/20* (2018.01); *C12Q 2600/158* (2013.01); *G01N 2800/26* (2013.01); *G01N 2800/60* (2013.01)

(58) Field of Classification Search
CPC ................................. C12Q 1/70; G16H 50/20
See application file for complete search history.

(56) References Cited

U.S. PATENT DOCUMENTS

| | | | |
|---|---|---|---|
| 10,913,068 B2 | 2/2021 | Chang et al. | |
| 2005/0221281 A1 | 10/2005 | Ho | |
| 2018/0245154 A1 | 8/2018 | Tsalik et al. | |
| 2019/0376969 A1* | 12/2019 | Burke | C07K 14/005 |

FOREIGN PATENT DOCUMENTS

| | | | |
|---|---|---|---|
| CN | 111041089 A | 4/2020 | |
| WO | 2018154075 A1 | 8/2018 | |
| WO | WO 2018/154075 * | 8/2018 | C12Q 1/68 |

OTHER PUBLICATIONS

Lu et al. (Journal of Medical Virology, 2021, p. 582-584).*
Doehn et al. (Infection, 2021, p. 757-762).*
Van Moorsel et al. (Frontiers in Medicine, May 16, 2020, p. 1-8).*
Ko et al. (International Journal of Antimicrobial Agents Mar. 2020, p. 1-3).*
International Search Report and the Written Opinion of the International Searching Authority corresponding to International Patent Application No. PCT/US2021/036961 mailed Oct. 21, 2021 (11 pages).
Kumar, Kiran, et al., "Presence of viral RNA of SARS-CoV-2 in conjunctival swab specimens of COVID-19 patients", Indian Journal of Ophthalmology [online]. 68(6): 1015-1017 (2020).
Tsalik, Ephraim L., et al., "Rapid, Sample-to-Answer Host Gene Expression Test to Diagnose Viral Infection", Open Forum Infectious Diseases. 6(11): ofz466 (2019).
Wang, Zhong, et al., "RNA-Seq: a revolutionary tool for transcriptomics", Nat Rev Genet. 10(1): 57-63 (2009).
"Normalizing Gene Expression Estimation", National Cancer Institute Center for Cancer Research, https://bioinformatics.ccr.cancer.gov/docs/bulk-rna-analysis-partek-flow/normalization/.
Qin, et al., "Effect of normalization on statistical and biological interpretation of gene expression profiles", Frontiers in Genetics 3:Article 160 (May 31, 2013) 11 pages.

* cited by examiner

*Primary Examiner* — Agnieszka Boesen
(74) *Attorney, Agent, or Firm* — Myers Bigel, P.A

(57) ABSTRACT

Provided are methods of making a SARS-CoV-2 (COVID-19) infection classifier for a platform, and optionally a non-COVID-19 viral infection classifier, a bacterial infection classifier, a non-infectious illness classifier, and/or a healthy subjects classifier for the platform. Methods and systems for determining the presence of SARS-CoV-2 (COVID-19) infection in a subject or for determining the viral stage of infection of a SARS-CoV-2 (COVID-19) illness in a subject suffering therefrom are also provided.

5 Claims, 2 Drawing Sheets

METHODS TO DETECT AND TREAT SARS-CoV-2 (COVID19) INFECTION

CROSS-REFERENCE TO RELATED APPLICATIONS

This application is a 35 U.S.C. § 371 national phase application of International Application Serial No. PCT/US2021/036961, filed Jun. 11, 2021, which claims the benefit of U.S. Provisional Patent Application No. 63/038,012, filed Jun. 11, 2020, and U.S. Provisional Patent Application No. 63/045,881, filed Jun. 30, 2020, the contents of each of which is incorporated by reference herein in its entirety.

CROSS-REFERENCE TO RELATED APPLICATIONS

This application claims the benefit of U.S. Provisional Patent Application No. 63/038,012, filed Jun. 11, 2020, and U.S. Provisional Patent Application No. 63/045,881, filed Jun. 30, 2020, the contents of each of which is incorporated by reference herein in its entirety.

BACKGROUND

Our understanding of the immune mechanisms driving the varied acute, recovery, and post-infectious manifestations of COVID-19 continues to evolve. Recent work has demonstrated altered mRNA profiles to SARS-CoV-2 infection at the site of infection—in respiratory epithelial cells, bronchoalveolar lavage, or nasal swab samples—highlighting the dysregulated and often hyperactive immune responses at local sites. However, non-respiratory tissues, specifically the circulating blood, play a significant role in controlling, propagating, and modulating these hyperactive responses. Hence, there is a need for the characterization of this peripheral response in blood to shed light on additional systemic manifestations, such as thrombosis, beyond the respiratory microenvironment. There is also a need to quickly and accurately determine the presence of a SARS-CoV-2 infection, to be able to differentiate it from other types of infection such as influenza, and to isolate and treat patients appropriately.

SUMMARY

Provided are methods of detecting the host transcriptional response in a biological sample such as peripheral blood of subjects with SARS-CoV-2 infection, and in some embodiments comparison to and distinguishing from other infections and healthy subjects to address this need.

The present disclosure provides, in part, a molecular diagnostic test that overcomes many of the limitations of current methods for distinguishing SARS-CoV-2 (COVID-19) infection against other acute respiratory infections (ARIs). The test detects the host's response to an acute respiratory infection (ARI) by measuring and analyzing the expression of a discrete set of genes, proteins or component peptides in a biological sample (e.g., peripheral blood sample). The genes, proteins or peptides in this "signature," revealed by statistical analysis, are differentially expressed in individuals presenting with SARS-CoV-2 as opposed with other ARIs (e.g., seasonal corona viral infections, bacterial pneumonia, influenza, etc.). Monitoring the host response to ARI using this multianalyte test in conjunction with analytic methods provides a classifier of high diagnostic accuracy and clinical utility, allowing health care providers to use the response of the host (the subject or patient) to reliably detect the presence or absence of a SARS-CoV-2 (COVID-19) infection and distinguish it from other ARIs. In some embodiments, the set of genes, proteins or component peptides (also referred to herein as gene products) comprise a plurality of those found in TABLE 7. In some embodiments, the set of gene products comprises a plurality of those found in TABLE 8.

Accordingly, one aspect of the present disclosure provides a method of making a SARS-CoV-2 (COVID-19) infection classifier for a platform, the method comprising, consisting of, or consisting essentially of: (a) obtaining biological samples from a plurality of subjects known to be suffering from COVID-19; (b) measuring on said platform the expression levels of a plurality of pre-defined gene products in said biological samples; (c) normalizing the gene product expression levels obtained in step (b) to generate normalized expression values; and (d) generating a SARS-CoV-2 (COVID-19) classifier for the platform based upon said normalized gene product expression values to thereby make the acute respiratory infection (ARI) classifier for the platform. In some embodiments, the classifier comprises one or more gene products found in TABLE 7. In other embodiments, the classifier comprises one or more gene products found in TABLE 8.

In some embodiments, the plurality of pre-defined gene products comprises 5, 10, 20, 30, 40, 50, 60, 70 or more of the weighted genes listed in TABLE 7. In some embodiments, the plurality of pre-defined gene products comprises 3, 5, 8, 10, 12, 14, 16, 18, or 20 of the weighted genes listed in TABLE 8. The weighted genes (i.e., those with a non-zero value) may be those weighted with respect to COVID-19, and/or include weighted genes with respect to the other infections/states reflected in the tables for comparison, especially when the other classifier(s) are made in the method.

In some embodiments, the measuring comprises, or is preceded by, one or more steps of: purifying cells, cellular materials, or secreted materials from said sample, preserving or disrupting the cells or cellular materials of said sample, and reducing complexity of sample through isolating or fractionating gene products from said sample.

In some embodiments, the measuring comprises quantitative or semi-quantitative direct detection or indirect detection using analyte specific reagents or methods.

In some embodiments, the analyte specific reagents are selected from the group consisting of antibodies, antibody fragments, aptamers, peptides and combinations thereof.

In some embodiments, the platform is selected from the group consisting of an array platform, a gene product analyte hybridization or capture platform, multi-signal coded detector platform, a mass spectrometry platform, an RNA sequencing platform, an amino acid sequencing platform, or a combination thereof.

In some embodiments, the generating comprises, consists of, or consists essentially of, iteratively: (i) assigning a weight for each normalized gene product expression value, entering the weight and expression value for each gene product into a classifier equation and determining a score for outcome for each of the plurality of subjects, then (ii) determining the accuracy of classification for each outcome across the plurality of subjects, and then (iii) adjusting the weight until accuracy of classification is optimized to provide said SARS-CoV-2 (COVID-19) infection classifier for the platform, wherein analytes having a non-zero weight are included in the respective classifier, and optionally uploading components of each classifier (gene product analytes, weights and/or etiology threshold value) onto one or more databases.

In some embodiments, the classifier is a linear regression classifier and said generating comprises converting a score of said classifier to a probability.

In some embodiments, the method further comprises validating said SARS-CoV-2 (COVID-19) infection classifier against a known dataset comprising at least two relevant clinical attributes, and optionally determining a threshold for the determination of SARS-CoV-2 infection.

In some embodiments, step (a) further comprises: obtaining biological samples from a plurality of subjects known to be suffering from a viral infection that is not COVID-19 (e.g. a coronavirus that is not SARS-CoV-2, and/or influenza), a bacterial infection, a non-infectious illness, and/or from a plurality of healthy subjects, and step (d) further comprises: generating a non-COVID-19 viral infection classifier, a bacterial infection classifier, a non-infectious illness classifier, and/or a healthy subjects classifier for the platform.

Another aspect of the present disclosure provides a method for determining the presence of SARS-CoV-2 (COVID-19) in a subject or for determining the viral stage of infection of a SARS-CoV-2 (COVID-19) infection in a subject suffering therefrom, comprising, consisting of, or consisting essentially of: (a) obtaining a biological sample from the subject; (b) measuring on a platform expression levels of a pre-defined set of gene products in said biological sample; (c) normalizing the gene product expression levels to generate normalized expression values; (d) entering the normalized gene product expression values into a SARS-CoV-2 (COVID-19) illness classifier, said classifier comprising pre-defined weighting values for each of the gene products of the pre-determined set of proteins and/or peptides for the platform, optionally wherein said classifier(s) are retrieved from one or more databases; and (e) calculating a presence or an etiology probability for the SARS-CoV-2 (COVID-19) infection based upon said normalized expression values and said classifier, and optionally determining a threshold for the determination of SARS-CoV-2 (COVID-19) infection, to thereby determine the presence of and/or the viral stage of a SARS-CoV-2 (COVID-19) infection in the subject.

In one embodiment, the classifier comprises at least one gene product found in TABLE 7. In another embodiment, the classifier comprises at least one gene product found in TABLE 8.

In some embodiments, the plurality of pre-defined gene products comprises 5, 10, 20, 30, 40, 50, 60, 70 or more of the weighted genes listed in TABLE 7. In some embodiments, the plurality of pre-defined gene products comprises 3, 5, 8, 10, 12, 14, 16, 18, or 20 of the weighted genes listed in TABLE 8. The weighted genes (i.e., those with a non-zero value) may be those weighted with respect to COVID-19, and/or include weighted genes with respect to the other infections/states reflected in the tables for comparison, especially when the other classifier(s) are used in the method.

In some embodiments, the classifier comprises a SARS-CoV-2 (COVID-19) illness classifier generated by a method as taught herein.

In some embodiments, the subject is exhibiting no symptoms of a SARS-CoV-2 (COVID-19) infection (i.e., determining the presence of a presymptomatic or asymptomatic infection).

In some embodiments, the method further comprises: (0 entering the normalized gene product expression values into one or more additional classifier(s) selected from a non-COVID-19 viral infection classifier, a bacterial infection classifier, a non-infectious illness classifier, and a healthy subjects classifier, said classifier(s) comprising pre-defined weighted values for each of the gene products of the plurality of pre-determined gene products for the platform, optionally wherein said classifier(s) is retrieved from one or more databases; and (g) calculating a presence or an etiology probability for the one or more additional classifier(s) based upon said normalized expression values, and optionally determining a threshold for the determination of a non-COVID-19 viral infection, a bacterial infection, a non-infectious illness, and/or a healthy status in the subject.

In some embodiments, the additional classifier(s) comprise an influenza infection classifier. In some embodiments, the additional classifier(s) comprise a non-COVID-19 coronavirus infection classifier. In some embodiments, the additional classifier(s) comprise a bacterial infection classifier.

In some embodiments, the method comprises monitoring the subject's response to a vaccine, drug or other antiviral therapy.

In some embodiments, the method further comprises administering to the subject an appropriate treatment regimen based on the etiology determined by the methods. In some embodiments, the appropriate treatment regimen comprises an antiviral therapy. In some embodiments, the appropriate treatment regimen comprises an anti-SARS-CoV-2 (COVID-19) therapy.

In some embodiments, the biological sample is selected from the group consisting of peripheral blood, sputum, nasal or nasopharyngeal swab, nasopharyngeal lavage, bronchoalveolar lavage, endotracheal aspirate, respiratory expectorate, respiratory epithelial cells or tissue, or other respiratory cell, tissue, or secretion samples and combinations thereof. In some embodiments, the biological sample comprises peripheral blood. In other embodiments, the biologic sample is obtained as a nasal or respiratory spray captured onto paper-based matrix for extraction or direct assay.

Another aspect of the present disclosure provides a SARS-CoV-2 (COVID-19) illness classifier comprising a plurality of the weighted gene products found in TABLE 7 or TABLE 8. In some embodiments, the classifier is made by the methods taught herein.

In some embodiments, the SARS-CoV-2 (COVID-19) infection classifier comprises: 5, 10, 20, 30, 40, 50, 60, 70 or more of the weighted genes listed in TABLE 7; or 5, 8, 10, 12 or 14 or more of the weighted genes listed in TABLE 8, wherein increased expression of the genes LY6E, IFIT1, OASL, IFI27, CCL2, LAMP3 indicate increased probability of COVID-19 infection, and increased expression of the genes SIGLEC1, RSAD2, GBP1, ISF15, IFIT5, DDX58, ATF3, and SEPT4 indicate decreased probability of COVID-19 infection.

Another aspect of the present disclosure provides a pan-SARS-CoV-2 (COVID-19) illness classifier, inclusive of virus variants, comprising at least one pan-viral gene product found in TABLE 7 or TABLE 8. Thus, the classifier using the host response to identify a SARS-CoV-2 infection as taught herein can detect variants of SARS-CoV-2 that might be missed by targeted viral assays like PCR.

Another aspect of the present disclosure provides a method of monitoring the response to a vaccine, drug or other antiviral therapy in a subject suffering from, or at risk of developing, a SARS-CoV-2 (COVID-19) illness, or for enriching a clinical trial of a therapy by verifying infection status, comprising determining a host response of said subject using a method as provided herein. In some embodiments, the drug is an antiviral drug. In some embodiments, the method may also include testing for the presence of a SARS-CoV-2 pathogen and/or variants or other pathogens (e.g. RSV, various flu strains), such as by a PCR assay to detect genetic material of the pathogen.

Other aspects of the present disclosure provides a kit for determining the presence or absence of SARS-CoV-2 (COVID-19) infection or illness in a subjector for distinguishing a SARS-CoV-2 (COVID-19) virus from another infection, the kit comprising, consisting of, or consisting essentially of: (a) a means for extracting a biological sample; (b) a means for generating one or more arrays consisting of a plurality of antibodies or other analyte specific reagents for use in measuring gene product expression levels of a pre-defined set of gene products; and (c) optionally, instructions for use.

Also provided is a system for determining the presence of SARS-CoV-2 (COVID-19) infection in a subject or for determining the viral stage of infection of a SARS-CoV-2 (COVID-19) illness in a subject suffering therefrom, and optionally one or more of a viral infection that is not COVID-19 (e.g., another coronavirus and/or an influenza), a bacterial infection, a non-infectious illness, and no infection or non-infectious illness (i.e. a healthy subject) comprising: at least one processor; a sample input circuit configured to receive a biological sample from the subject; a sample analysis circuit coupled to the at least one processor and configured to determine gene expression levels of the biological sample; an input/output circuit coupled to the at least one processor; a storage circuit coupled to the at least one processor and configured to store data, parameters, and/or classifiers; and a memory coupled to the processor and comprising computer readable program code embodied in the memory that when executed by the at least one processor causes the at least one processor to perform operations comprising: controlling/performing measurement via the sample analysis circuit of gene expression levels of a pre-defined set of genes in said biological sample; normalizing the gene expression levels to generate normalized gene expression values; retrieving from the storage circuit a SARS-CoV-2 (COVID-19) infection classifier, and optionally also one or more of a non-COVID-19 viral infection classifier (e.g., another coronavirus, and/or an influenza), a bacterial infection classifier, a non-infectious illness classifier, and a healthy subjects classifier, said classifier(s) comprising pre-defined weighted values (i.e., coefficients) for each of the genes of the pre-defined set of genes; entering the normalized gene expression values into the classifier(s); calculating an etiology probability for one or more of a SARS-CoV-2 (COVID-19) infection, a non-COVID-19 viral infection, a bacterial infection, a non-infectious illness, and a healthy subject based upon said classifier(s); and controlling output via the input/output circuit of a determination of the presence of SARS-CoV-2 (COVID-19) infection in a subject or for determining the viral stage of infection of a SARS-CoV-2 (COVID-19) illness, and optionally one or more of a non-COVID-19 viral infection (e.g., another coronavirus, an influenza), a bacterial infection, a non-infectious illness, and a healthy subject.

In some embodiments, the system comprises computer readable code to transform quantitative, or semi-quantitative, detection of gene expression to a cumulative score or probability.

In some embodiments, the system comprises an array platform, a thermal cycler platform (e.g., multiplexed and/or real-time PCR platform), a hybridization and multi-signal coded (e.g., fluorescence) detector platform, a nucleic acid mass spectrometry platform, a nucleic acid sequencing platform, or a combination thereof.

In some embodiments, the pre-defined set of genes comprises 10, 20, 30, 40, 50 or more of the weighted genes listed in TABLE 7. In some embodiments, the pre-defined set of genes comprises 5, 8, 10, 12 or 14 or more of the weighted genes listed in TABLE 8.

In some embodiments, the classifier(s) were generated by a method as taught herein.

Also provided is a SARS-CoV-2 (COVID-19) infection classifier as taught herein for use in a method of diagnosis for a SARS-CoV-2 (COVID-19) infection as taught herein.

BRIEF DESCRIPTION OF THE DRAWINGS

The accompanying Figures and Examples are provided by way of illustration and not by way of limitation. The foregoing aspects and other features of the disclosure are explained in the following description, taken in connection with the accompanying example figures (also "FIG.") relating to one or more embodiments, in which.

DETAILED DESCRIPTION

Figure 1:
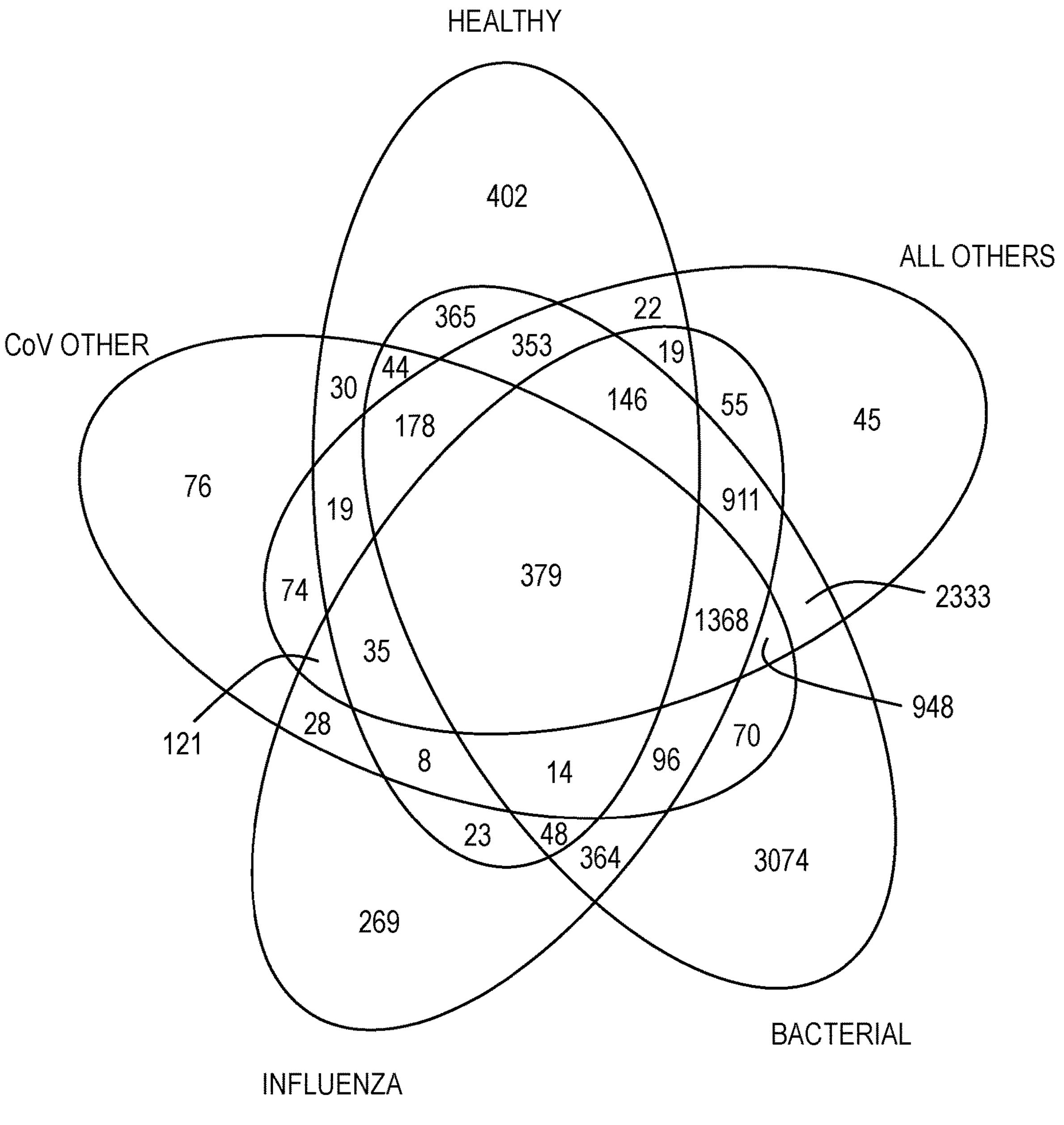
FIG. 1 presents a Venn Diagram showing the number of overlapping genes differentially expressed between COVID-19 subjects, influenza, bacterial infection, healthy controls, or all others combined. Genes shown represent those with adjusted p values of $<0.05$.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e., at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations when interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a feature such as a signature comprises components A, B and C, it is specifically intended that any of A, B or C, or a combination thereof, can be omitted and disclaimed singularly or in any combination.

The present disclosure provides that alterations in gene, protein and metabolite expression in blood in response to pathogen exposure can be used to identify and characterize the etiology of the infection in a subject with a high degree of accuracy.

Definitions

As used herein, the term "signature" refers to a set of biological analytes and the measurable quantities of said analytes whose expression level signifies the presence or absence of the specified biological state. These signatures may be determined in a plurality of subjects with known infection status (e.g. a confirmed SARS-CoV-2 (COVID-19) viral infection, or lacking SARS-CoV-2 (COVID-19) virus infection), and are discriminative (individually or jointly) of one or more categories or outcomes of interest. These measurable quantities, also known as biological markers, can be (but are not limited to) gene expression levels, protein or peptide levels, or metabolite levels.

In some embodiments, a "signature" may comprise a particular combination of gene products whose expression levels, when incorporated into a classifier as taught herein, discriminate a condition such as a SARS-CoV-2 (COVID-19) infection. The term "SARS-CoV-2 (COVID-19) gene product expression levels," "viral SARS-CoV-2 (COVID-19) signature," and "SARS-CoV-2 (COVID-19) signature" are used interchangeably and refer to the level of gene products, for example, such as those found in the Examples. The altered expression of one or more of these gene products is indicative of the subject having aSARS-CoV-2 (COVID-19) infection. In some embodiments, the signature is able to distinguish individuals with infection due to SARS-CoV-2 (COVID-19) from individuals lacking infection or infected with a non-SARS-CoV-2 (COVID-19) pathogen.

As used herein, the term "gene product" refers to any biochemical material resulting from the expression of a gene. Examples include, but are not limited to, nucleic acids such as RNA and mRNA, proteins, component peptides, expressed proteomes, epitopes, and any subsets thereof, and combinations thereof.

The term "genetic material" refers to a material used to store genetic information in the nuclei or mitochondria of an organism's cells, or derivatives thereof. Examples of genetic material include, but are not limited to double-stranded and single-stranded DNA, cDNA, RNA, mRNA, or their encoded products.

As used herein, the terms "classifier" and "predictor" are used interchangeably and refer to a mathematical function that uses the values of the signature (e.g. gene expression levels or protein and/or peptide levels from a defined set of gene products) and a pre-determined coefficient for each signature component to generate scores for a given observation or individual patient for the purpose of assignment to a category. A classifier is linear if scores are a function of summed signature values weighted by a set of coefficients. Furthermore, a classifier is probabilistic if the function of signature values generates a probability, a value between 0 and 1.0 (or 0 and 100%) quantifying the likelihood that a subject or observation belongs to a particular category or will have a particular outcome, respectively. Probit regression and logistic regression are examples of probabilistic linear classifiers.

A classifier, including a linear classifier, may be obtained by a procedure known as training, which consists of using a set of data containing observations with known category membership. Specifically, training seeks to find the optimal coefficient (or weight) for each component of a given signature, where the optimal result is determined by the highest classification accuracy. In some embodiments, a unique classifier may be developed and trained with respect to a particular platform upon which the signature is measured. See also US Publication 2018/0245154 to Tsalik et al., which is incorporated by reference herein.

Classification is the activity of assigning an observation or a patient to one or more categories or outcomes (e.g. a patient is infected with SARS-CoV-2 (COVID-19) or is not infected). In some cases, an observation or a patient may be classified to more than one category, e.g. in case of co-infection. The outcome, or category, is determined by the value of the scores provided by the classifier, when such predicted values are compared to a cut-off or threshold value or limit. In other scenarios, the probability of belonging to a particular category may be given if the classifier reports probabilities.

"Platform" or "technology" as used herein refers to an apparatus (e.g., instrument and associated parts, computer, computer-readable media comprising one or more databases as taught herein, reagents, etc.) that may be used to measure a signature, e.g., gene expression levels, in accordance with the present disclosure. Examples of platforms include, but are not limited to, an array hybridization platform, a nucleic acid sequencing platform, a thermocycler platform (e.g., multiplexed and/or real-time polymerase chain reaction (PCR) platform [e.g., a TaqMan® Array Cards, a Biocartis Idyll™ sample-to-result technology, etc.] or "droplet" digital PCR [e.g. Bio-Rad RainDance Digital PCR or Fluidigm Biomark HD) or an isothermal amplification and detection platform (using, for example, reverse transcription loop mediated isothermal amplification, Rolling circle amplification, Recombinase polymerase amplification, Helicase-dependent amplification), a gene product hybridization or capture platform (e.g., a protein and/or peptide hybridization or capture platform), a multi-signal coded (e.g., fluorescence) detector platform, etc., a mass spectrometry platform, an amino acid sequencing platform, a magnetic resonance platform, and combinations thereof. A nucleic acid sequencing platform may include next-generation sequencing-by-synthesis (SBS) technologies (e.g. Illumina SBS), single molecule nanopore sequencing technologies (e.g. Oxford Nanopore Technologies MinION™ and GridION™) and nanopore sequencing of modified or surrogate molecules (e.g. Roche SBX™). In some embodiments, the platforms may comprise a gene product hybridization or capture platform, a multi-signal coded (e.g., fluorescence) detector platform, etc., a gene product sequencing platform, and any combination or combinations thereof.

In some embodiments, the platform is configured to measure gene product (e.g., RNA transcript, protein, or peptide) expression levels semi-quantitatively; that is, rather than measuring in discrete or absolute expression, the expression levels are measured as an estimate and/or relative to each other or a specified marker or markers (e.g., expression of another, "standard" or "reference" gene product [e.g., RNA, protein or peptide]).

In some embodiments, semi-quantitative measuring includes immunodetection methods including ELISA or protein arrays, which utilize analyte specific immuno-reagents to provide specificity for particular protein or peptide sequence and/or structure, coupled with signal detection modalities such as fluorescence or luminescence to provide the estimated or relative expression levels of the genes within the signature. An array-based immunoassay platform may include, for example, the MesoScaleDiscovery (MSD) platform for measurement of multiple analytes per well, configured as antibody "spots" in each assay well. The MSD platform utilizes chemiluminescent reagents activated upon electrical stimulation, or "electrochemiluminescence" detection.

The terms "array," "microarray" and "micro array" are interchangeable and refer to an arrangement of a collection of reagents presented on a substrate. Any type of array can be utilized in the methods provided herein. For example, arrays can be on a solid "planar" substrate (a solid phase array), such as a glass slide, or on a semi-solid substrate, such as nitrocellulose membrane. Arrays can also be presented on beads, i.e., a bead array. These beads are typically microscopic and may be made of, e.g., polystyrene. The array can also be presented on nanoparticles, which may be made of, e.g., particularly gold, but also silver, palladium, or platinum. Magnetic nanoparticles may also be used. Other examples include nuclear magnetic resonance microcoils. The analyte specific reagents can be antibody or antibody fragments or nucleic acid aptamers, for example. The arrays may additionally comprise other compounds, such as nucleic acids, peptides, proteins, cells, chemicals, carbohydrates, and the like that specifically bind proteins, peptides, or metabolites.

A hybridization and multi-signal coded detector platform includes, for example, NanoString nCounter® technology, in which hybridization of a color-coded barcode attached to a target-specific probe (e.g., barcoded antibody probe) is detected; and Luminex xMAP technology, in which microsphere beads are color coded and coated with a target-specific reagents (e.g., color-coded beads coated with analyte-specific antibody) probe for detection.

Gene products may also be measured using mass spectrometry. For example, protein and/or peptide mass spectrometry (MS) utilizes instruments capable of accurate mass determination and includes a variety of instruments and methods. In some embodiments, the measurement by MS is performed using two primary methods: electrospray ionization (ESI) and matrix-assisted laser desorbtion/ionization (MALDI). Proteins may be analyzed either as "top-down" approach characterizing intact proteins, or a "bottom up" approach characterizing digested protein fragments or peptides. Protein or peptide MS may be performed in conjunction with up-front methods to reduce complexity of biological samples, such as gel electrophoresis or liquid chromatography. Resulting MS data can be used to identify and quantify specific proteins and/or peptides.

The term "computer readable medium" refers to any device or system for storing and providing information (e.g., data and instructions) to a computer processor. Examples of computer readable media include, but are not limited to, DVDs, CDs hard disk drives, magnetic tape and servers for streaming media over networks, and applications, such as those found on smart phones and tablets. In various embodiments, aspects of the present invention including data structures and methods may be stored on a computer readable medium. Processing and data may also be performed on numerous device types, including but not limited to, desk top and lap top computers, tablets, smart phones, and the like.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

As used herein, the term "biological sample" comprises any sample that may be taken from a subject that contains genetic material or products thereof (e.g. mRNA, proteins or peptides) that can be used in the methods provided herein. For example, a biological sample may comprise a peripheral blood sample. The term "peripheral blood sample" refers to a sample of blood circulating in the circulatory system or body taken from the system of body. Other samples may comprise those taken from the upper respiratory tract, including but not limited to, sputum, nasopharyngeal swab and nasopharyngeal wash. A biological sample may also comprise those samples taken from the lower respiratory tract, including but not limited to, bronchoalveolar lavage and endotracheal aspirate. A biological sample may also comprise any combination thereof.

The terms "subject" and "patient" are used interchangeably herein and refer to both human and non-human animals. The term "non-human animals" of the disclosure includes all vertebrates, e.g., mammals and non-mammals, such as non-human primates, sheep, dog, cat, horse, cow, chickens, amphibians, reptiles, and the like. In some embodiments, the subject is suffering from, at risk of developing, or has suffered from an infection with SARS-CoV-2 (COVID-19).

As used herein, the terms "treat", "treatment" and "treating" refer to the reduction or amelioration of the severity, duration and/or progression of a disease or disorder or one or more symptoms thereof resulting from the administration of one or more therapies. Such terms may refer to a reduction in the replication of a virus (e.g., SARS-CoV-2 (COVID-19)), or a reduction in the spread of a virus to other organs or tissues in a subject or to other subjects. Such terms also may refer to the reduction of symptoms by suppression of host response to the infecting organism. Treatment may include therapies for SARS-CoV-2 (COVID-19) resulting from non-infectious illness, such as allergy treatment, asthma treatments, and the like. In some embodiments, the treatment comprises an antiviral treatment.

The term "effective amount" refers to an amount of a therapeutic agent that is sufficient to exert a physiological effect in the subject. The term "responsivity" refers to a change in gene product levels of genes in a subject in response to the subject being infected with a virus (e.g., SARS-CoV-2 (COVID-19)) compared to the gene expression levels of the genes in a subject that is not infected with a virus (e.g., SARS-CoV-2 (COVID-19)), or a control subject. In certain embodiments, the genes comprise those found in the Examples.

The term "appropriate treatment regimen" refers to the standard of care needed to treat a specific disease or disorder. Often such regimens require the act of administering to a subject a therapeutic agent(s) capable of producing a curative effect, or lessening of symptoms or duration, in a disease state. In some embodiments, a therapeutic agent or combination of agents for treating a subject having a viral infection (e.g., SARS-CoV-2 (COVID-19)) may include, but is not limited to, oseltamivir, remdesivir, RNAi antivirals, inhaled ribavirin, monoclonal antibody antibodies such as casirivimab, imdevimab, bamlanivimab or etesevimabrespigam, zanamivir, and neuraminidase blocking agents, convalescent plasma, or treatments for symptoms due to viral infection such as dexamethasone or anticoagulation drugs. The invention contemplates the use of the methods of the invention with treatments such as antibiotics, antivirals or antibacterial agents antibiotics that are not yet available. In some embodiments, a therapeutic agent or combination of agents for treating a subject having a viral infection (e.g., Sars-CoV-2 (COVID19)) and or a bacterial infection includes, but is not limited to penicillin, macrolide, beta-lactam, cephalosporin, fluoroquinolone, tetracycline, or trimethoprim/sulfamethoxazole drugs.

Appropriate treatment regimens may also include treatments for viral infections resulting from non-infectious illness, such as allergy treatments, including but not limited to, administration of antihistamines, decongestants, anticholinergic nasal sprays, leukotriene inhibitors, mast cell inhibitors, steroid nasal sprays etc. and asthma treatments, including but not limited to, inhaled corticosteroids, leukotriene modifiers, long-acting beta agonists, combinations inhalers (e.g., fluticasone-salmeterol; budesonide-formoterol; mometasone-formoterol, etc.), theophylline, short-acting beta agonists, ipratropium, oral and intravenous corticosteroids, omalizumab and the like. Further examples of such therapeutic agents include, but are not limited to, NSAIDS, acetaminophen, anti-histamines, beta-agonists, anti-tussives, CXCR2 antagonists (e.g., Danirixin), or other medicaments that reduce the symptoms associated with the disease process.

Methods of Generating a Sars-CoV-2 Classifier and Uses Thereof

The present disclosure provides, in part, a molecular diagnostic test that overcomes many of the limitations of current methods for distinguishing SARS-CoV-2 (COVID-19) infection against other acute respiratory infections (ARIs). The test can detect the host's response to an acute respiratory infection (ARI) by measuring and analyzing the expression of a discrete set of gene products in a biological sample (e.g., peripheral blood sample). The gene products in this "signature," revealed by statistical analysis, are differentially expressed in individuals presenting with SARS-CoV-2 as compared to other ARIs (e.g., seasonal corona viral infections, bacterial pneumonia, influenza, etc.). Monitoring the host response to ARI using this multianalyte test, which may be performed in conjunction with analytic methods, provides a classifier of high diagnostic accuracy and clinical utility, allowing health care providers to use the response of the host (the subject or patient) to reliably detect the presence or absence of a SARS-CoV-2 (COVID-19) infection and distinguish it from other ARIs. In some embodiments, the set of gene products comprise at least one of those found in TABLE 7. In some embodiments, the set of gene products comprise at least one of those found in TABLE 8.

Accordingly, one aspect of the present disclosure provides a method of making a SARS-CoV-2 (COVID-19) illness classifier for a platform, the method comprising, consisting of, or consisting essentially of: (a) obtaining biological samples from a plurality of subjects known to be suffering from COVID19; (b) measuring on said platform the expression levels of a plurality of pre-defined gene products in said biological samples; (c) normalizing the gene product expression levels obtained in step (b) to generate normalized expression values; and (d) generating a SARS-CoV-2 (COVID-19) classifier for the platform based upon said normalized gene product expression values to thereby make the acute respiratory infection (ARI) classifier for the platform. In some embodiments, the classifier comprises one or more gene products found in TABLE 7. In other embodiments, the classifier comprises one or more gene products found in TABLE 8.

In some embodiments, the measuring comprises, or is preceded by, one or more steps of: purifying cells, cellular materials, or secreted materials from said sample, preserving or disrupting the cells or cellular materials of said sample, and reducing complexity of sample through isolating or fractionating gene products from said sample.

In another embodiment, the measuring comprises quantitative or semi-quantitative direct detection or indirect detection using analyte specific reagents or methods.

In some embodiments, the measuring comprises the detection and quantification (e.g., semi-quantification) of mRNA in the sample. In some embodiments, the gene expression levels are adjusted relative to one or more standard gene level(s) ("normalized"). As known in the art, normalizing is done to remove technical variability inherent to a platform to give a quantity or relative quantity (e.g., of expressed genes).

In another embodiment, the analyte specific reagents are selected from the group consisting of antibodies, antibody fragments, aptamers, peptides and combinations thereof.

In other embodiments, the platform is selected from the group consisting of an array platform, a gene product analyte hybridization or capture platform, multi-signal coded detector platform, a mass spectrometry platform, an amino acid sequencing platform, or a combination thereof.

In another embodiment, the generating comprises, consists of, or consists essentially of, iteratively: (i) assigning a weight for each normalized gene product expression value, entering the weight and expression value for each gene product into a classifier equation and determining a score for outcome for each of the plurality of subjects, then (ii) determining the accuracy of classification for each outcome across the plurality of subjects, and then (iii) adjusting the weight until accuracy of classification is optimized to provide said SARS-CoV-2 (COVID-19) for the platform, wherein analytes having a non-zero weight are included in the respective classifier, and optionally uploading components of each classifier (gene product analytes, weights and/or etiology threshold value) onto one or more databases.

In another embodiment, the classifier is a linear regression classifier and said generating comprises converting a score of said classifier to a probability.

In other embodiments, the method further comprises validating said SARS-CoV-2 (COVID-19) illness classifier against a known dataset comprising at least two relevant clinical attributes, and optionally determining a threshold for the determination of SARS-CoV-2 illness.

Another aspect of the present disclosure provides a method for determining the presence of SARS-CoV-2 (COVID-19) in a subject or for determining the viral stage of infection of a SARS-CoV-2 (COVID-19) illness in a subject suffering therefrom, comprising, consisting of, or consisting essentially of: (a) obtaining a biological sample from the subject; (b) measuring on a platform expression levels of a pre-defined set of gene products in said biological sample; (c) normalizing the gene product expression levels to generate normalized expression values; (d) entering the normalized gene product expression values into one or more SARS-CoV-2 (COVID-19) illness classifiers, said classifier(s) comprising pre-defined weighting values for each of the gene products of the pre-determined set of proteins and/or peptides for the platform, optionally wherein said classifier(s) are retrieved from one or more databases; and (e) calculating a presence or an etiology probability for the SARS-CoV-2 (COVID-19) illness based upon said normalized expression values and said classifier(s), and optionally determining a threshold for the determination of SARS-CoV-2 (COVID-19) illness, to thereby determine the presence of a ARI in the subject or the viral stage of infection of a SARS-CoV-2 (COVID-19) illness in the subject.

In one embodiment, the classifier comprises at least one gene product found in TABLE 7. In another embodiment, the classifier comprises at least one gene product found in TABLE 8.

Another aspect of the present disclosure provides a method for determining whether a subject is at risk of developing a SARS-CoV-2 (COVID-19) illness, or for determining the presence of a latent or subclinical or presymptomatic SARS-CoV-2 (COVID-19) infection in a subject exhibiting no symptoms, comprising, consisting of, or consisting essentially of: (a) obtaining a biological sample from the subject; (b) measuring on a platform expression levels of a pre-defined set of gene products in said biological sample; (c) normalizing the gene product expression levels to generate normalized expression values; (d) entering the normalized gene product expression values into one or more acute respiratory virus illness classifiers, said classifier(s) comprising pre-defined weighting values for each of the gene products of the pre-determined set of proteins and/or peptides for the platform, optionally wherein said classifier(s) are retrieved from one or more databases; and (e) calculating a risk probability or a probability for one or more of SARS-CoV-2 (COVID-19) illness based upon said normalized expression values and said classifier(s), and optionally determining a threshold for the determination of SARS-CoV-2 (COVID-19) illness, to thereby determine whether the subject is a risk of developing a SARS-CoV-2 (COVID-19) illness, or to determine the presence of a latent SARS-CoV-2 (COVID-19) infection in the subject.

In one embodiment, the classifier comprises at least one gene product found in TABLE 7. In another embodiment, the classifier comprises at least one gene product found in TABLE 8.

Another aspect of the present disclosure provides a method for determining the etiology of an acute respiratory infection in a subject suffering therefrom, comprising: (a) obtaining a biological sample from the subject; (b) measuring on a platform expression levels of a pre-defined set of gene products in said biological sample; (c) normalizing the gene product expression levels to generate normalized expression values; (d) entering the normalized gene product expression values into one or more acute respiratory infection classifiers, said classifier(s) comprising pre-defined weighting values for each of the gene products of the pre-determined set of proteins and/or peptides for the platform, optionally wherein said classifier(s) are retrieved from one or more databases; and (e) calculating a presence or an etiology probability for one or more of the ARI based upon said normalized expression values and said classifier(s), and optionally determining a threshold for the determination of ARI, to thereby determine the etiology of an ARI in the subject.

In some embodiments, the etiology of the ARI is determined to be SARS-CoV-2 (COVID-19). In one embodiment, the classifier comprises at least one gene product found in TABLE 7. In another embodiment, the classifier comprises at least one gene product found in TABLE 8.

In some embodiments, the biological sample is selected from the group consisting of peripheral blood, sputum, nasal or nasopharyngeal swab, nasopharyngeal lavage, bronchoalveolar lavage, endotracheal aspirate, respiratory expectorate, respiratory epithelial cells or tissue, or other respiratory cell, tissue, or secretion samples and combinations thereof. In some embodiments, the biological sample comprises peripheral blood. In other embodiments, the biologic sample is obtained as a nasal or respiratory spray captured onto paper-based matrix for extraction or direct assay.

In some embodiments, detection and quantification of mRNA may first involve a reverse transcription and/or amplification step, e.g., RT-PCR such as quantitative RT-PCR or an isothermal amplification method. In some embodiments, detection and quantification may be based upon the unamplified mRNA molecules present in or purified from the biological sample. Direct detection and measurement of RNA molecules typically involves hybridization to complementary primers and/or labeled probes. Such methods include traditional northern blotting and surface-enhanced Raman spectroscopy (SERS), which involves shooting a laser at a sample exposed to surfaces of plasmonic-active metal structures with gene-specific probes, and measuring changes in light frequency as it scatters.

Similarly, detection of RNA derivatives, such as cDNA, typically involves hybridization to complementary primers and/or labeled probes. This may include high-density oligonucleotide probe arrays (e.g., solid state microarrays and bead arrays) or related probe-hybridization methods, and polymerase chain reaction (PCR)-based amplification and detection, including real-time, digital, and end-point PCR methods for relative and absolute quantitation of specific RNA molecules.

Additionally, sequencing-based methods can be used to detect and quantify RNA or RNA-derived material levels. When applied to RNA, sequencing methods are referred to as RNAseq, and provide both qualitative (sequence, or presence/absence of an RNA, or its cognate cDNA, in a sample) and quantitative (copy number) information on RNA molecules from a sample. See, e.g., Wang et al. 2009 Nat. Rev. Genet. 10(1):57-63. Another sequence-based method, serial analysis of gene expression (SAGE), uses cDNA "tags" as a proxy to measure expression levels of RNA molecules.

Moreover, use of proprietary platforms for mRNA detection and quantification may also be used to complete the methods of the present disclosure. Examples of these are Pixel™ System, incorporating Molecular Indexing™, developed by CELLULAR RESEARCH, INC., NanoString® Technologies nCounter gene expression system; mRNA-Seq, Tag-Profiling, BeadArray™ technology and VeraCode from Illumina, the ICEPlex System from PrimeraDx, and the QuantiGene 2.0 Multiplex Assay from Affymetrix.

As an example, RNA from whole blood from a subject can be collected using RNA preservation reagents such as PAXgene™ Blood RNA tubes (PreAnalytiX, Valencia, Calif.), RNAlater (QIAGEN), ETDA using, e.g., BD Vacutainer® EDTA blood collection tube, or a capillary blood collection may be used, e.g., a BD Microtainer®. Other chemical denaturing and/or stabilizing reagents may also be used (e.g. guanidinium isothiocyanate or similar reagents). RNA can be extracted using a standard PAXgene™ RNA (QIAGEN) extraction protocol, or using other nucleic acid capture or concentration methods. Additional processing steps to reduce abundant and non-interesting transcripts may be included, such as reduction of abundant blood globin transcripts using, for example, GLOBINClear™ (Ambion, Austin, Tex.) or capture of poly-adenylated mRNAs using oligo-dT binding methods (depletes abundant ribosomal RNAs and other non-protein coding nucleic acids). Depending on the technology, removal of abundant and non-interesting transcripts may increase the sensitivity of the assay, such as with a microarray or sequencing platform.

Quality of the RNA can be assessed by several means. For example, RNA quality can be assessed using an Agilent 2100 Bioanalyzer immediately following extraction. This analysis provides an RNA Integrity Number (RIN) as a quantitative measure of RNA quality. Also, following globin reduction the samples can be compared to the globin-reduced standards. In addition, the scaling factors and background can be assessed following hybridization to microarrays.

Real-time PCR may be used to quickly identify gene expression from a whole blood sample. For example, the isolated RNA can be reverse transcribed and then amplified and detected in real time using non-specific fluorescent dyes that intercalate with the resulting ds-DNA, or sequence-specific DNA probes labeled with a fluorescent reporter which permits detection only after hybridization of the probe with its complementary DNA target.

Hence, it should be understood that there are many methods of mRNA quantification and detection that may be used by a platform in accordance with the methods disclosed herein.

The expression levels are typically normalized following detection and quantification as appropriate for the particular platform using methods routinely practiced by those of ordinary skill in the art.

Another aspect of the present disclosure provides a SARS-CoV-2 (COVID-19) infection classifier comprising at least one gene product found in TABLE 7.

Another aspect of the present disclosure provides a SARS-CoV-2 (COVID-19) infection classifier comprising at least one gene product found in TABLE 8.

In another embodiment, the methods further comprise administering to the subject an appropriate treatment regimen based on the etiology determined by the methods provided herein. In some embodiments, the appropriate treatment regimen comprises an antiviral therapy. In certain embodiments, the appropriate treatment regimen comprises an anti-SARS-CoV-2 (COVID-19) therapy.

Another aspect of the present disclosure provides a method of monitoring the response to a vaccine, drug or other antiviral therapy in a subject suffering from, or at risk of developing, a SARS-CoV-2 (COVID-19) illness comprising determining a host response of said subject using a method as provided herein. In some embodiments, the drug is an antiviral drug.

Other aspects of the present disclosure provides a kit for determining the presence or absence of SARS-CoV-2 (COVID-19) illness in a subject, or for detecting the presence or absence of a SARS-CoV-2 (COVID-19) virus in a subject, or for distinguishing a SARS-CoV-2 (COVID-19) virus from another acute respiratory infection (ARI), the kit comprising, consisting of, or consisting essentially of: (a) a means for extracting a biological sample; (b) a means for generating one or more arrays consisting of a plurality of antibodies or other analyte specific reagents for use in measuring gene product expression levels of a pre-defined set of gene products; and (c) optionally, instructions for use. In some embodiments, the means for extracting a biological sample may include a syringe for extracting a blood sample, and/or a suitable container (e.g., sterile container such as a cup or tube) for receiving the sample. In some embodiments, the means for generating one or more arrays may comprise a microfluidic, "lab-on-a-chip" device. See, e.g., U.S. Pat. No. 10,913,068 to Chang et al.; and U.S. Publication No. 2005/0221281 to Ho.

Classification Systems

Figure 2:
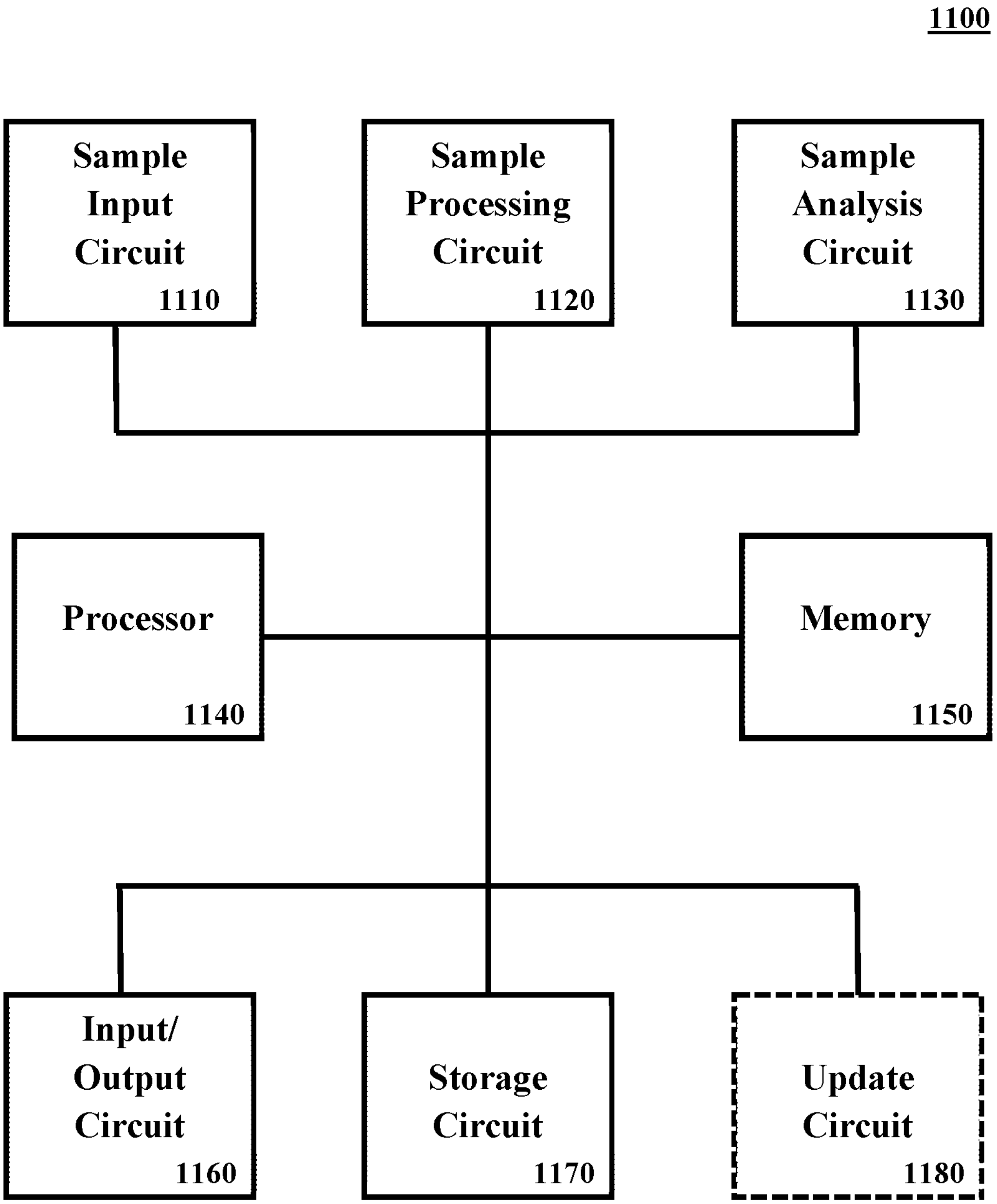
FIG. 2 is a block diagram of a classification system and/or computer program product that may be used in a platform in accordance with the present invention. A classification system and/or computer program product 1100 may include a processor subsystem 1140, including one or more Central Processing Units (CPU) on which one or more operating systems and/or one or more applications run. While one processor 1140 is shown, it will be understood that multiple processors 1140 may be present, which may be either electrically interconnected or separate. Processor(s) 1140 are configured to execute computer program code from memory devices, such as memory 1150, to perform at least some of the operations and methods described herein. The storage circuit 1170 may store databases which provide access to the data/parameters/classifiers used by the classification system 1110 such as the signatures, weights, thresholds, etc. An input/output circuit 1160 may include displays and/or user input devices, such as keyboards, touch screens and/or pointing devices. Devices attached to the input/output circuit 1160 may be used to provide information to the processor 1140 by a user of the classification system 1100. Devices attached to the input/output circuit 1160 may include networking or communication controllers, input devices (keyboard, a mouse, touch screen, etc.) and output devices (printer or display). An optional update circuit 1180 may be included as an interface for providing updates to the classification system 1100 such as updates to the code executed by the processor 1140 that are stored in the memory 1150 and/or the storage circuit 1170. Updates provided via the update circuit 1180 may also include updates to portions of the storage circuit 1170 related to a database and/or other data storage format which maintains information for the classification system 1100, such as the signatures, weights, thresholds, etc. The sample input circuit 1110 provides an interface for the classification system 1100 to receive biological samples to be analyzed. The sample processing circuit 1120 may further process the biological sample within the classification system 1100 so as to prepare the biological sample for automated analysis.

With reference to FIG. 2, a classification system and/or computer program product 1100 may be used in or by a platform, according to various embodiments described herein. A classification system and/or computer program product 1100 may be embodied as one or more enterprise, application, personal, pervasive and/or embedded computer systems that are operable to receive, transmit, process and store data using any suitable combination of software, firmware and/or hardware and that may be standalone and/or interconnected by any conventional, public and/or private, real and/or virtual, wired and/or wireless network including all or a portion of the global communication network known as the Internet, and may include various types of tangible, non-transitory computer readable medium.

As shown in FIG. 2, the classification system 1100 may include a processor subsystem 1140, including one or more Central Processing Units (CPU) on which one or more operating systems and/or one or more applications run. While one processor 1140 is shown, it will be understood that multiple processors 1140 may be present, which may be either electrically interconnected or separate. Processor(s) 1140 are configured to execute computer program code from memory devices, such as memory 1150, to perform at least some of the operations and methods described herein, and may be any conventional or special purpose processor, including, but not limited to, digital signal processor (DSP), field programmable gate array (FPGA), application specific integrated circuit (ASIC), and multi-core processors.

The memory subsystem 1150 may include a hierarchy of memory devices such as Random Access Memory (RAM), Read-Only Memory (ROM), Erasable Programmable Read-Only Memory (EPROM) or flash memory, and/or any other solid state memory devices.

A storage circuit 1170 may also be provided, which may include, for example, a portable computer diskette, a hard disk, a portable Compact Disk Read-Only Memory (CDROM), an optical storage device, a magnetic storage device and/or any other kind of disk- or tape-based storage subsystem. The storage circuit 1170 may provide non-volatile storage of data/parameters/classifiers for the classification system 1100. The storage circuit 1170 may include disk drive and/or network store components. The storage circuit 1170 may be used to store code to be executed and/or data to be accessed by the processor 1140. In some embodiments, the storage circuit 1170 may store databases which provide access to the data/parameters/classifiers used for the classification system 1110 such as the signatures, weights, thresholds, etc. Any combination of one or more computer readable media may be utilized by the storage circuit 1170. The computer readable media may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. As used herein, a computer readable storage medium may be any tangible medium that can contain, or store a program for use by or in connection with an instruction execution system, apparatus, or device.

An input/output circuit 1160 may include displays and/or user input devices, such as keyboards, touch screens and/or pointing devices. Devices attached to the input/output circuit 1160 may be used to provide information to the processor 1140 by a user of the classification system 1100. Devices attached to the input/output circuit 1160 may include networking or communication controllers, input devices (keyboard, a mouse, touch screen, etc.) and output devices (printer or display). The input/output circuit 1160 may also provide an interface to devices, such as a display and/or printer, to which results of the operations of the classification system 1100 can be communicated so as to be provided to the user of the classification system 1100.

An optional update circuit 1180 may be included as an interface for providing updates to the classification system 1100. Updates may include updates to the code executed by the processor 1140 that are stored in the memory 1150 and/or the storage circuit 1170. Updates provided via the update circuit 1180 may also include updates to portions of the storage circuit 1170 related to a database and/or other data storage format which maintains information for the classification system 1100, such as the signatures, weights, thresholds, etc.

The sample input circuit 1110 of the classification system 1100 may provide an interface for the platform as described hereinabove to receive biological samples to be analyzed. The sample input circuit 1110 may include mechanical elements, as well as electrical elements, which receive a biological sample provided by a user to the classification system 1100 and transport the biological sample within the classification system 1100 and/or platform to be processed. The sample input circuit 1110 may include a bar code reader that identifies a bar-coded container for identification of the sample and/or test order form. The sample processing circuit 1120 may further process the biological sample within the classification system 1100 and/or platform so as to prepare the biological sample for automated analysis. The sample analysis circuit 1130 may automatically analyze the processed biological sample. The sample analysis circuit 1130 may be used in measuring, e.g., gene expression levels of a pre-defined set of genes with the biological sample provided to the classification system 1100. The sample analysis circuit 1130 may also generate normalized gene expression values by normalizing the gene expression levels. The sample analysis circuit 1130 may retrieve from the storage circuit 1170 a SARS-CoV-2 (COVID-19) infection classifier, and optionally also one or more of a viral infection classifier that is not a COVID-19 classifier, a bacterial infection classifier, a non-infectious illness classifier, and a healthy subjects classifier. The sample analysis circuit 1130 may enter the normalized gene expression values into the classifier(s). The sample analysis circuit 1130 may calculate an etiology probability for a SARS-CoV-2 (COVID-19) infection, and optionally also one or more of a viral infection that is not COVID-19 (e.g., another coronavirus, an influenza), a bacterial infection, a non-infectious illness, and a healthy subject based upon said classifier(s) and control output, via the input/output circuit 1160.

The sample input circuit 1110, the sample processing circuit 1120, the sample analysis circuit 1130, the input/output circuit 1160, the storage circuit 1170, and/or the update circuit 1180 may execute at least partially under the control of the one or more processors 1140 of the classification system 1100. As used herein, executing "under the control" of the processor 1140 means that the operations performed by the sample input circuit 1110, the sample processing circuit 1120, the sample analysis circuit 1130, the input/output circuit 1160, the storage circuit 1170, and/or the update circuit 1180 may be at least partially executed and/or directed by the processor 1140, but does not preclude at least a portion of the operations of those components being separately electrically or mechanically automated. The processor 1140 may control the operations of the classification system 1100, as described herein, via the execution of computer program code.

Computer program code for carrying out operations for aspects of the present disclosure may be written in any combination of one or more programming languages, including an object oriented programming language such as Java, Scala, Smalltalk, Eiffel, JADE, Emerald, C++, C #, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the classification system 1100, partly on the classification system 1100, as a stand-alone software package, partly on the classification system 1100 and partly on a remote computer or entirely on the remote computer or server. In the latter scenario, the remote computer may be connected to the classification system 1100 through any type of network, including a local area network (LAN) or a wide area network (WAN), or the connection may be made to an external computer (for example, through the Internet using an Internet Service Provider) or in a cloud computer environment or offered as a service such as a Software as a Service (SaaS).

In some embodiments, the system includes computer readable code that can transform quantitative, or semi-quantitative, detection of gene expression to a cumulative score or probability of the etiology of a SARS-CoV-2 (COVID-19) infection, and optionally also one or more of a viral infection that is not COVID-19 (e.g., another coronavirus, an influenza), a bacterial infection, a non-infectious illness, and a healthy subject.

In some embodiments, the system is a sample-to-result system, with the components integrated such that a user can simply insert a biological sample to be tested, and some time later (preferably a short amount of time, e.g., 30 or 45 minutes, or 1, 2, or 3 hours, up to 8, 12, 24 or 48 hours) receive a result output from the system.

It is to be understood that the invention is not limited in its application to the details of construction and the arrangement of components set forth in the following description or illustrated in the following drawings. The invention is capable of other embodiments and of being practiced or of being carried out in various ways.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

Another aspect of the present disclosure provides all that is described and illustrated herein.

The following Examples are provided by way of illustration and not by way of limitation.

EXAMPLES

Transcriptomic Responses in Circulating Leukocytes Define Mechanisms of Dysregulated Immunity During SARS-CoV-2 Infection RNA sequencing on peripheral blood samples from subjects with COVID-19 was performed to better define the complex, heterogeneous and dysregulated host response to SARS-CoV-2. It was found that SARS-CoV-2 triggers a robust and conserved early inflammatory response that is heavily interferon-driven but also marked by early B-cell activation and antibody production. Heterogeneous dysregulation of coagulation and fibrinolytic pathways are present in early COVID-19, as were IL1 and JAK/STAT signaling pathways, that persist into late disease. Classifiers were developed based on these differentially expressed genes, which are capable of differentiating SARS-CoV-2 infection from other acute viral illnesses with high accuracy (auROC 0.94). The transcriptome in peripheral blood reveals critical aspects of the immune response in COVID-19 and offers a novel biomarker approach to diagnosis, severity prediction, and elucidation of key dysregulated pathways.

Methods

Over the initial months of the COVID-19 outbreak in North Carolina, we enrolled 49 individuals with PCR-proven, symptomatic SARS-CoV-2 infection, 14 of which were sampled at multiple times. Subjects were enrolled when they presented for clinical care, and the time from symptom onset was recorded for each individual sample collected (range 1-35 days). Most were outpatients at the time of enrollment, although 20% had disease requiring hospital admission, and 4 required ICU level care. Subjects with COVID-19 were further divided based on time from symptom onset (early<11 days, middle 11-21 days, late>21 days). As comparators, we included banked PAXgene preserved blood RNA samples from patients presenting to the Emergency Department with acute respiratory infection (ARI) with adjudicated diagnoses of seasonal coronavirus infections (n=49), influenza (n=17), bacterial pneumonia (n=23), and healthy matched controls (n=19).

We performed RNA sequencing on peripheral blood samples to measure gene expression at each COVID19 timepoint and across various disease states. Peripheral blood was collected in PAXgene™ Blood RNA tubes (PreAnalytiX), and total RNA extracted using the PAXgene™ Blood miRNA Kit (QIAGEN) employing the manufacturer's recommended protocol. RNA quantity and quality were assessed using Nanodrop 2000 spectrophotometer (ThermoFisher) and Bioanalyzer 2100 with RNA 6000 Nano Chips (Agilent).

RNA Sequencing data was normalized using the frozen RMA method. Batch-correct was performed using Combat. Models were fit using regularized regression implemented in the glmnet R package. Differential gene expression was then measured across the various outcome categories within a given clinical outcome categorization method (recovery phenotype approach and expected recovery differential approach).

The data demonstrated that regardless of time of illness, SARS-CoV-2 infection triggered a robust response in circulating PBMCs compared to healthy subjects and other infections (FIG. 1). However, the response to SARS-CoV-2 varied based on the length of antecedent illness. At early times (<10d of symptoms), the host response of most patients was dominated by upregulation of interferon-response signals that are broadly similar to those described for other common viral ARIs7-10 (e.g., IFI27, IFI44L, Ly6E and others).

Interferon-stimulated genes (ISG) were expressed at a higher level than in subjects with seasonal CoV infection but lower than in subjects with influenza. These transcriptional responses were associated with COVID19 disease duration and viral load, declining over time but more slowly than is seen with other common viruses. Additionally, while these ISGs were tightly co-expressed in seasonal CoV and influenza infections, they exhibited bimodal expression in early SARS-CoV-2. Most ISGs (e.g., IFI27, IFI44L) were highly unregulated while others (ATF3, LAMP3, SEPT4, TNFAP6, IFIT5) were dissociated from the common ISG response and appeared relatively suppressed in SARS-CoV-2. This pattern of Type I IFN dysregulation is consistent with prior observations in SARS-CoV and MERS infections.

In addition to an altered interferon-response, subjects with early symptomatic COVID-19 exhibited marked activation of B-cell and immunoglobulin production genes—not just compared to healthy controls, but also to seasonal CoV and influenza infections. This distinct transcriptomic manifestation of humoral activation pathways occurred as early as one day after symptom onset and was conserved throughout the recovery phase—as long as 35 days from the start of symptoms. B-cell and immunoglobulin gene activation corresponded to serum IgA expression as early as 4 days into clinical disease, specific serum IgG expression by day 8, and an early rise in the proportion of plasmablasts relative to other viral infections.

We also noted transcriptomic manifestations of biological pathways in COVID19 samples that are of particular clinical interest. SARS-CoV-2 infection is associated with thrombotic events perhaps due to a hyperinflammatory state, which led to recommendations for venous thromboembolism prophylaxis in hospitalized patients with COVID-19. Compared to other seasonal CoV and influenza, we observed marked upregulation of a genomic signature of VTE17 and increased expression of many thrombotic pathway genes in a subset of early COVID-19 cases. This included prekallikrein (KLKB1), plasminogen activator inhibitor (SERPINE1), urokinase receptor (PLAUR), and others (FIG. 1*g*), along with decreased expression of antithrombotic protein S (PROS). During late COVID-19, as far as 35 days after symptom onset, this altered signal persisted in a subset of individuals, albeit at a lower level than during acute disease.

A number of immunomodulatory drugs are being explored to treat inflammatory manifestations of COVID-19. We therefore determined whether the inflammatory pathways targeted by these investigational drugs demonstrated altered gene expression in COVID-19. In a subset of mild-moderate infections, there was marked upregulation of IL1 and JAK/STAT signaling pathways compared to other infections that often persisted through late disease, although no difference in IL6 signaling was seen. The heterogeneity of activation of these pathways across subjects suggests that pharmacogenomic approaches may prove useful to determine which patients may be most appropriate for a given immunomodulatory approach to mitigate symptom severity, and thus should be explored further.

To develop an RNA classifier for COVID19, we used linear regression modeling to discover a 'signature' of expressed genes that best differentiates COVID-19 from other infections, cumulatively across the disease spectrum and at different illness stages. Even when considering COVID-19 subjects across a wide range of clinical duration (1 to 35 days from symptom onset), there were conserved RNA changes compared to subjects with other respiratory infections and healthy controls. We discovered a gene expression signature that differentiated subjects with SARS-CoV-2 infection at any time from all others with a high degree of accuracy (auROC 0.91). This was, in part, driven by B-cell activation and immunoglobulin production that began early in COVID-19 and persisted throughout the observed course. See TABLE 7.

Additionally, we and others have previously identified signatures consisting primarily of interferon-stimulated genes that accurately identify acute respiratory viral infection across a broad array of seasonal viruses. Our previously reported 'panviral' signature accurately identifies subjects exposed to respiratory viral pathogens but not yet showing symptoms, often before detectable viral shedding is present. In the current dataset, this 'panviral' signature highly accurately identified the presence or absence of symptomatic SARS-CoV-2 infection (auROC 0.94). See TABLE 8.

Notably, with a change in the relative weights and coefficients of the model, measurement of these exact genes can also be utilized to accurately diagnose and separate COVID-19, seasonal coronavirus, or influenza infections. The potential for this approach is profound, as measurement of expression levels of a single small set of genes could allow both for detection of SARS-CoV-2 infection as well as simultaneously giving information about the presence of other viral (or even bacterial) infections. Also, since similar sets of genes permit early, presymptomatic detection of influenza and seasonal coronavirus infections, it is reasonable to extrapolate that tests based broadly on this approach may offer similar early detection of COVID-19 in exposed individuals. Successful demonstration of presymptomatic COVID-19 detection could contribute to outbreak surveillance and quarantine decisions for asymptomatic but potentially contagious hosts that may drive much of the spread of this disease, once properly validated in exposed but presymptomatic subjects.

TABLE 1

Cohort Descriptions

Cohort Sizes

| | COVID-19 | healthy | CoV other | Influenza | Bacterial | Total |
|---|---|---|---|---|---|---|
| Subjects | 47 | 19 | 49 | 17 | 33 | 155 |
| Samples | 78 | 19 | 59 | 17 | 23 | 196 |

Number of Weeks since Symptom Onset

| | 1 week | 2 weeks | 3 weeks | 4 weeks | 5 weeks |
|---|---|---|---|---|---|
| Samples | 4 | 22 | 20 | 13 | 9 |

TABLE 1-continued

| Cohort Descriptions | | | | | |
|---|---|---|---|---|---|
| Pathogen by Cohort | | | | | |
| | COVID-19 | healthy | CoV other | Influenza | Bacterial |
| Corona OC43 | 0 | 0 | 2 | 0 | 0 |
| Coronavirus | 0 | 0 | 48 | 0 | 0 |
| Coronavirus 229E | 0 | 0 | 1 | 0 | 0 |
| Coronavirus HKU1 | 0 | 0 | 5 | 0 | 0 |
| Coronavirus NL63 | 0 | 0 | 1 | 0 | 0 |
| Coronavirus OC43 | 0 | 0 | 2 | 0 | 0 |
| COVID-19 | 78 | 0 | 0 | 0 | 0 |
| *Enterobacter aerogenes* | 0 | 0 | 0 | 0 | 1 |
| Haemophilus influenza | 0 | 0 | 0 | 0 | 3 |
| healthy | 0 | 19 | 0 | 0 | 0 |
| Influenza A 2009 H1N1 | 0 | 0 | 0 | 16 | 0 |
| Influenza A | 0 | 0 | 0 | 1 | 0 |
| Polymicrobial | 0 | 0 | 0 | 0 | 4 |
| *Staphylococcus aureus* | 0 | 0 | 0 | 0 | 2 |
| *Streptococcus pneumoniae* | 0 | 0 | 0 | 0 | 13 |

TABLE 2

Univariate Testing: COVID-19 vs. Healthy
Negative logFC corresponds to genes up-regulated in 'COVID-19'.
Positive logFC corresponds to genes up-regulated in 'Healthy'.

| | logFC | AveExpr | t | P. Value | adj. P. Val | B |
|---|---|---|---|---|---|---|
| RPL34 | 3.08 | 3.55 | 12.14 | 0.00 | 0.00 | 47.66 |
| TMA7 | 1.84 | 4.02 | 11.01 | 0.00 | 0.00 | 39.97 |
| RP11.466H18.1 | 3.06 | 0.60 | 10.50 | 0.00 | 0.00 | 35.56 |
| RPS24 | 2.46 | 5.71 | 10.49 | 0.00 | 0.00 | 36.50 |
| UBE2Q2P6 | 3.06 | 1.43 | 10.40 | 0.00 | 0.00 | 35.17 |
| RPL31 | 2.73 | 4.86 | 10.01 | 0.00 | 0.00 | 33.32 |
| RPL7P9 | 2.50 | 1.09 | 9.83 | 0.00 | 0.00 | 31.38 |
| RPL26 | 1.93 | 2.05 | 9.81 | 0.00 | 0.00 | 31.65 |
| RF11.543P15.1 | 2.21 | 2.24 | 9.39 | 0.00 | 0.00 | 29.15 |
| GA85 | 1.49 | 4.03 | 9.39 | 0.00 | 0.00 | 29.28 |

TABLE 3

Univariate Testing: COVID-19 vs. Other Coronavirus
Negative logFC corresponds to genes up-regulated in 'COVID-19'.
Positive logFC corresponds to genes up-regulated in 'Other Coronavirus'.

| | logFC | AveExpr | t | P. Value | adj. P. Val. | B |
|---|---|---|---|---|---|---|
| RPL36AL | −1.02 | 6.62 | −7.99 | 0.00 | 0.00 | 20.58 |
| MRPL51 | −1.06 | 4.45 | −7.78 | 0.00 | 0.00 | 19.11 |
| STX11 | 0.93 | 6.58 | 7.46 | 0.00 | 0.00 | 17.53 |
| PARP14 | 1.11 | 8.22 | 7.13 | 0.00 | 0.00 | 15.68 |
| SORT1 | 0.77 | 5.95 | 7.12 | 0.00 | 0.00 | 15.59 |
| TRANK1 | 0.77 | 7.91 | 7.05 | 0.00 | 0.00 | 15.21 |
| NDUFA1 | −1.07 | 4.29 | −7.01 | 0.00 | 0.00 | 14.81 |
| RNF213 | 0.91 | 9.51 | 6.98 | 0.00 | 0.00 | 14.87 |
| WARS | 0.92 | 8.24 | 6.97 | 0.00 | 0.00 | 14.81 |
| AFF1 | 1.00 | 5.76 | 6.80 | 0.00 | 0.00 | 13.86 |

TABLE 4

Univariate Testing: COVID-19 vs. Influenza
Negative logFC corresponds to genes up-regulated in 'COVID-19'.
Positive logFC corresponds to genes up-regulated in 'Influenza'.

| | logFC | AveExpr | t | P. Value | adj. P. Val. | B |
|---|---|---|---|---|---|---|
| USP18 | 3.96 | 2.68 | 13.37 | 0.00 | 0.00 | 55.92 |
| SPATS2L | 3.69 | 3.71 | 12.69 | 0.00 | 0.00 | 51.42 |
| RTP4 | 2.57 | 3.42 | 12.27 | 0.00 | 0.00 | 48.50 |
| CXCR2P1 | 2.36 | 4.80 | 11.68 | 0.00 | 0.00 | 44.57 |
| TCN2 | 2.37 | 4.12 | 11.27 | 0.00 | 0.00 | 41.78 |
| HERC6 | 2.40 | 4.65 | 11.24 | 0.00 | 0.00 | 41.60 |
| GRAMD1B | 1.93 | 4.32 | 11.02 | 0.00 | 0.00 | 40.07 |
| CMPK2 | 3.81 | 4.58 | 10.98 | 0.00 | 0.00 | 39.80 |
| TRIM5 | 2.03 | 5.17 | 10.85 | 0.00 | 0.00 | 38.94 |
| KIAA0226 | 1.33 | 6.31 | 10.70 | 0.00 | 0.00 | 37.94 |

TABLE 5

Univariate Testing: COVID-19 vs. Bacterial
Negative logFC corresponds to genes up-regulated in 'COVID-19'.
Positive logFC corresponds to genes up-regulated in 'Bacterial'.

| | logFC | AveExpr | t | P. Value | adj. P. Val. | B |
|---|---|---|---|---|---|---|
| SORT1 | 2.89 | 5.95 | 22.56 | 0.00 | 0.00 | 118.33 |
| IRAK3 | 3.82 | 5.94 | 22.26 | 0.00 | 0.00 | 116.43 |
| GYG1 | 3.12 | 5.87 | 21.85 | 0.00 | 0.00 | 113.86 |
| NLRC4 | 2.47 | 5.35 | 21.56 | 0.00 | 0.00 | 111.94 |
| GAS7 | 2.31 | 7.45 | 21.17 | 0.00 | 0.00 | 109.49 |
| AGFG1 | 2.49 | 5.83 | 20.61 | 0.00 | 0.00 | 105.83 |
| MKNK1 | 2.34 | 6.98 | 20.61 | 0.00 | 0.00 | 105.84 |
| PFKFB3 | 3.80 | 6.41 | 20.32 | 0.00 | 0.00 | 104.00 |
| CD55 | 2.57 | 7.53 | 20.04 | 0.00 | 0.00 | 102.10 |
| ACVR1B | 2.07 | 4.73 | 19.70 | 0.00 | 0.00 | 99.80 |

TABLE 6

Univariate Testing: COVID-19 vs. All Others
Negative logFC corresponds to genes up-regulated in 'COVID-19'.
Positive logFC corresponds to genes up-regulated in 'All others'.

| | logFC | AveExpr | t | P. Value | adj. P. Val. | B |
|---|---|---|---|---|---|---|
| PRR7 | −0.64 | 3.59 | −8.43 | 0.00 | 0.00 | 23.05 |
| CPTP | −0.49 | 5.58 | −8.17 | 0.00 | 0.00 | 21.76 |
| PTP4A3 | −1.01 | 5.85 | −8.14 | 0.00 | 0.00 | 21.59 |
| PPIB | −0.64 | 7.99 | −8.13 | 0.00 | 0.00 | 21.48 |
| UBL4A | −0.48 | 5.45 | −8.07 | 0.00 | 0.00 | 21.13 |
| STX11 | 0.98 | 6.58 | 8.02 | 0.00 | 0.00 | 20.82 |
| ABF1 | 1.15 | 5.76 | 7.99 | 0.00 | 0.00 | 20.64 |
| DDX60L | 1.41 | 6.57 | 7.90 | 0.00 | 0.00 | 20.15 |
| RNPEPL1 | −0.46 | 8.90 | −7.85 | 0.00 | 0.00 | 19.80 |
| BAP1 | −0.31 | 6.70 | −7.84 | 0.00 | 0.00 | 19.77 |

TABLE 7

Genes and associated coefficients (i.e. weights) for diagnosis of COVID-19 and other infections.

| Gene | COVID-19 | healthy | CoV other | Influenza | Bacterial |
|---|---|---|---|---|---|
| AKT2 | 1.122954 | 0 | 0 | 0 | 0 |
| LPCAT1 | 1.021566 | 0 | 0 | 0 | 0 |
| CACNA1I | 0.764902 | 0 | 0 | 0 | 0 |
| HEATR5B | −0.73643 | 0 | 0 | 0 | 0 |
| PTMAP5 | 0.674936 | 0 | 0 | 0 | 0 |
| TRAF6 | −0.56863 | 0 | 0 | 0 | 0 |
| TMEM184B | 0.508982 | 0 | 0 | 0 | 0 |
| C15orf52 | 0.364032 | 0 | 0 | 0 | 0 |
| PIF1 | 0.258137 | 0 | 0 | 0 | 0 |
| NIDI | −0.24949 | 0 | 0 | 0 | 0 |
| RPL36AL | 0.210556 | 0 | 0 | 0 | 0 |
| RHOB | 0.202214 | 0 | 0 | 0 | 0 |
| AOAH.IT1 | −0.19546 | 0 | 0 | 0 | 0 |
| KLHDC8B | 0.192266 | 0 | 0 | 0 | 0 |
| RP11.925D8.3 | −0.18363 | 0 | 0 | 0 | 0 |
| CETN2 | 0.182543 | 0 | 0 | 0 | 0 |
| FAM13A.AS1 | −0.15939 | 0 | 0 | 0 | 0 |
| PCGF3 | −0.15389 | 0 | 0 | 0 | 0 |
| MDGA1 | −0.14958 | 0 | 0 | 0 | 0 |
| IGHV1.24 | 0.134092 | 0 | 0 | 0 | 0 |
| KEAP1 | 0.119483 | 0 | 0 | 0 | 0 |
| CTD.2047H16.3 | −0.11344 | 0 | 0 | 0 | 0 |
| HORMAD1 | −0.10871 | 0 | 0 | 0 | 0 |
| PDHB | 0.108133 | 0 | 0 | 0 | 0 |
| MRAS | −0.07935 | 0 | 0 | 0 | 0 |
| PRRG4 | −0.07468 | 0 | 0 | 0 | 0 |
| CTD.2357A8.2 | −0.07095 | 0 | 0 | 0 | 0 |
| HNRNPA1P21 | 0.065862 | 0 | 0 | 0 | 0 |
| CD70 | 0.064254 | 0 | 0 | 0 | 0 |
| RP11.358B23.7 | −0.05828 | 0 | 0 | 0 | 0 |
| BIRC5 | 0.057247 | 0 | 0 | 0 | 0 |
| NKX3.1 | 0.051037 | 0 | 0 | 0 | 0 |
| ZFHX3 | −0.04962 | 0 | 0 | 0 | 0 |
| HOXA.AS2 | 0.045888 | 0 | 0 | 0 | 0 |
| TBC1D19 | 0.044055 | 0 | 0 | 0 | 0 |
| RP11.180M15.7 | −0.03832 | 0 | 0 | 0 | 0 |
| IGHG1 | 0.036451 | 0 | 0 | 0 | 0 |
| PTRF | 0.035431 | 0 | 0 | 0 | 0 |
| PTGES3P1 | −0.03265 | 0 | 0 | 0 | 0 |
| IGKV1.9 | 0.028673 | 0 | 0 | 0 | 0 |
| ZNF607 | −0.02271 | 0 | 0 | 0 | 0 |
| ENSG00000282458 | 0.022201 | 0 | 0 | 0 | 0 |
| IGHGP | 0.016327 | 0 | 0 | 0 | 0 |
| RP13.270P17.3 | −0.01584 | 0 | 0 | 0 | 0 |
| NRG1 | −0.0152 | 0 | 0.095214 | 0 | 0 |
| NUTM2B.AS1 | −0.01247 | 0 | 0 | 0 | 0 |
| ENSG00000282416 | −0.0083 | 0 | 0 | 0 | 0 |
| RP11.861A13.3 | −0.00745 | 0 | 0 | 0 | 0 |
| RP11.81H14.2 | 0.005412 | 0 | 0 | 0 | 0 |
| RP11.707O23.5 | 0.004433 | 0 | 0 | 0 | 0 |
| KIAA2018 | −0.0038 | 0 | 0 | 0 | 0 |
| PM20D1 | 0.001792 | 0 | 0 | 0 | 0 |

TABLE 7-continued

Genes and associated coefficients (i.e. weights) for diagnosis of COVID-19 and other infections.

| Gene | COVID-19 | healthy | CoV other | Influenza | Bacterial |
|---|---|---|---|---|---|
| TREML4 | −0.00046 | 0 | 0 | 0 | 0 |
| IFI6 | 0 | 0 | 0.194711 | 0 | 0 |
| BSDC1 | 0 | 0 | −1.25321 | 0 | 0 |
| MYCL | 0 | 0 | 0.057357 | 0 | 0 |
| CYP2J2 | 0 | 0 | −0.09966 | 0.004564 | 0 |
| PRPF38B | 0 | 0 | 0 | 0 | 0.419765 |
| SMG5 | 0 | 0 | −0.34371 | 0 | 0 |
| CD1E | 0 | 0 | 0.043355 | 0 | 0 |
| FLVCR1 | 0 | 0 | 0.532653 | 0 | 0 |
| TRIB2 | 0 | 0 | 0 | 0.609624 | 0 |
| CD302 | 0 | 0 | 0 | −0.30176 | 0 |
| EEF1B2 | 0 | 0.01203 | 0 | 0 | 0 |
| CXCR2P1 | 0 | 0 | 0 | 0.098215 | 0 |
| FAM124B | 0 | 0 | 0.066905 | 0 | 0 |
| HMGB1P5 | 0 | 0 | −0.14487 | 0 | 0 |
| TMA7 | 0 | 0.34788 | 0 | 0 | 0 |
| COX17 | 0 | 0 | −0.01331 | 0 | 0 |
| IL20RB | 0 | 0 | 0.007127 | 0 | 0 |
| KIAA0226 | 0 | 0 | 0 | 0.275263 | 0 |
| RP11.696N14.1 | 0 | 0 | −0.00415 | 0 | 0 |
| FAM105A | 0 | 0 | 0 | 0 | 0.37178 |
| WDR55 | 0 | 0 | −0.22946 | 0 | 0 |
| GNPDA1 | 0 | 0 | 0 | 0.27628 | 0 |
| FLT4 | 0 | 0 | 0 | −0.01094 | 0 |
| SERPINB9 | 0 | 0 | 0.003236 | 0 | 0 |
| HIST1H2BF | 0 | 0 | −0.18972 | 0 | 0 |
| RP1.34B20.4 | 0 | 0 | −0.08091 | 0 | 0 |
| HIST1H2BH | 0 | 0 | −0.16685 | 0 | 0 |
| HIST1H2BO | 0 | 0 | −0.01524 | 0 | 0 |
| HLA.B | 0 | 0 | 0.58078 | 0 | 0 |
| DPRXP2 | 0 | −0.13041 | 0 | 0 | 0 |
| CDKN1A | 0 | 0 | 0 | 0.581738 | 0 |
| PDE7B | 0 | 0 | 0.042871 | 0 | 0 |
| CPVL | 0 | 0 | 0.150252 | 0 | 0 |
| ZNF3 | 0 | 1.205241 | 0 | 0 | 0 |
| PMPCB | 0 | 1.077919 | 0 | 0 | 0 |
| NRCAM | 0 | 0 | 0.05909 | 0 | 0 |
| LINC00998 | 0 | 0 | 0 | −0.04436 | 0 |
| TRBV4.2 | 0 | 0 | 0 | 0 | −0.20421 |
| AP1S2 | 0 | 0 | 0.138528 | 0 | 0 |
| ALAS2 | 0 | 0 | 0.229026 | 0 | 0 |
| NONO | 0 | 0 | 0.061114 | 0 | 0 |
| XIST | 0 | 0 | 0.000707 | 0 | 0 |
| CHRNA2 | 0 | 0 | −0.0046 | 0 | 0 |
| MSC | 0 | 0 | −0.38368 | 0 | 0 |
| RP11.363E7.4 | 0 | 0 | 0.070497 | 0 | 0 |
| KIAA1045 | 0 | 0 | 0 | −0.0219 | 0 |
| FXN | 0 | 0 | 0 | 0 | −0.28815 |
| FBXW2 | 0 | 0 | 0 | 0 | 0.311334 |
| PSMD5.AS1 | 0 | 0 | −0.14983 | 0 | 0 |
| ARAP1.AS2 | 0 | 0 | 0.010495 | 0 | 0 |
| CWC15 | 0 | 0 | −0.38279 | 0 | 0 |
| SIDT2 | 0 | 0 | 0 | 1.342787 | 0 |
| RPS24 | 0 | 0.402703 | 0 | 0 | 0 |
| RP1.197B17.4 | 0 | 0 | 0.034128 | 0 | 0 |
| TROAP | 0 | −0.08166 | 0 | 0 | 0 |
| PTGES3 | 0 | −0.82412 | 0 | 0 | 0 |
| RP11.244J10.1 | 0 | 0.307503 | 0 | 0 | 0 |
| LTA4H | 0 | 0 | 0 | 0 | 0.569169 |
| RPL6 | 0 | 0.92353 | 0 | 0 | 0 |
| HRK | 0 | 0 | 0.10598 | 0 | 0 |
| RNASEH2B | 0 | 0 | 0 | 0 | −0.09294 |
| TMCO3 | 0 | 0 | 0 | 0 | 0.03144 |
| TRDV2 | 0 | 0 | 0.040764 | 0 | 0 |
| SNW1 | 0 | 0 | −0.57094 | 0 | 0 |
| GOLGA5 | 0 | 0 | −0.48207 | 0 | 0 |
| IFI27 | 0 | −0.05083 | 0 | 0.098792 | 0 |
| CASC5 | 0 | −0.22866 | 0 | 0 | 0 |
| AAGAB | 0 | 0 | −0.03047 | 0 | 0 |
| IL34 | 0 | 0 | 0.233922 | 0 | 0 |
| TNFSF12 | 0 | 0 | 0.586247 | 0 | 0 |
| RAPGEFL1 | 0 | 0 | 0 | −0.1466 | 0 |
| LUC7L3 | 0 | 0 | −0.46165 | 0 | 0 |
| MAFG | 0 | 0 | 0 | 0 | 0.336472 |
| THBD | 0 | 0 | 0 | −0.10614 | 0 |

TABLE 7-continued

Genes and associated coefficients (i.e. weights) for diagnosis of COVID-19 and other infections.

| Gene | COVID-19 | healthy | CoV other | Influenza | Bacterial |
|---|---|---|---|---|---|
| RPL37AP1 | 0 | 0 | −0.08096 | 0 | 0 |
| PI3 | 0 | 0 | 0 | −0.32033 | 0 |
| VAPB | 0 | 0 | 0 | 0 | 0.508849 |
| RETN | 0 | 0 | 0 | 0 | 0.029746 |
| LRP3 | 0 | 0 | 0 | −0.45879 | 0 |
| C19orf84 | 0 | 0 | −0.12282 | 0 | 0 |
| CACNG6 | 0 | 0 | 0 | 0 | −0.0028 |
| RIMBP3 | 0 | −0.02046 | 0 | 0 | 0 |
| H1F0 | 0 | −0.56793 | 0 | 0.008748 | 0 |
| PWP2 | 0 | −0.05205 | 0 | 0 | 0 |
| C21orf33 | 0 | 0 | 0.112425 | 0 | 0 |
| MT.CO3 | 0 | 0 | 0.025763 | 0 | 0 |

TABLE 8

Genes and associated coefficients (i.e. weights) for diagnosis of COVID-19 and other infections.

| Gene | COVID-19 | healthy | CoV other | Influenza | Bacterial |
|---|---|---|---|---|---|
| LY6E | 2.238371 | 0 | 0 | 0 | 0 |
| IFIT1 | 1.891102 | 1.412406 | 0 | 0 | −0.31161 |
| SIGLEC1 | −1.36441 | 0.388108 | 0 | 0 | 0 |
| RSAD2 | −1.20483 | 0 | 0.171663 | 0 | 0 |
| OASL | 0.709628 | 0 | 0 | 0 | 0 |
| GBP1 | −0.63075 | 0 | 0.126779 | 0 | 0 |
| ISG15 | −0.62858 | 0.58357 | 0 | 0 | 0 |
| IFIT5 | −0.49208 | 0 | 0.009058 | 0 | 0 |
| IFI27 | 0.348549 | −0.32924 | −0.05761 | 0.829187 | 0 |
| CCL2 | 0.304575 | 0 | −0.09873 | 0 | 0.102489 |
| LAMP3 | 0.2298 | −0.12208 | 0 | 0.269435 | −0.29635 |
| DDX58 | −0.2146 | 0 | 0 | 0 | 0 |
| ATF3 | −0.16335 | 0 | −0.04608 | 0.32514 | 0 |
| SEPT4 | −0.12384 | 0 | −0.06124 | 0 | 0 |
| IFI6 | 0 | 0 | 0.760158 | −0.74914 | 0 |
| IFI44 | 0 | 1.030131 | −0.65546 | 0 | 0 |
| TNFAIP6 | 0 | 0.465419 | −0.0131 | −0.30751 | 2.257092 |
| RTP4 | 0 | 0.185752 | −1.00099 | 0 | −1.10157 |
| SERPING1 | 0 | −0.52381 | 0 | 0 | 0 |
| IFIT2 | 0 | 0 | −0.15663 | 0.658299 | 0 |
| IFIT3 | 0 | 0 | 2.155756 | 0 | 0 |
| OAS3 | 0 | −3.15587 | 0 | 0.843723 | 0 |
| XAF1 | 0 | 0 | −0.5357 | 1.00892 | 0 |

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present invention is well adapted to carry out the objects and obtain the ends and advantages mentioned, as well as those inherent therein. The present disclosures described herein are presently representative of preferred embodiments, are exemplary, and are not intended as limitations on the scope of the invention. Changes therein and other uses will occur to those skilled in the art which are encompassed within the spirit of the invention as defined by the scope of the claims.

We claim:

1. A method for determining the presence of SARS-COV-2 (COVID-19) infection in a subject or for determining the viral stage of infection of a SARS-CoV-2 (COVID-19) illness in a subject suffering therefrom, comprising:

(a) obtaining a biological sample from the subject;

(b) measuring on a platform expression levels of a plurality of pre-defined set of gene products in said biological sample, wherein the plurality of pre-defined gene products comprises;

(i) 10, 20, 30, 40, 50 or more of the genes:

AKT2,
LPCAT1,
CACNA1I,
HEATR5B,
PTMAP5,
TRAF6,
TMEM184B,
C15orf52,
PIF1,
NID1,
RPL36AL,
RHOB,
AOAH.IT1,
KLHDC8B,
RP11.925D8.3,
CETN2,
FAM13A.AS1, PCGF3,
MDGA1,
IGHV1.24,
KEAP1,
CTD.2047H16.3,
HORMAD1,
PDHB,
MRAS,
PRRG4,
CTD.2357A8.2,
HNRNPA1P21,
CD70,
RP11.358B23.7,
BIRC5,
NKX3.1,
ZFHX3,
HOXA.AS2,
TBC1D19,
RP11.180M15.7,
IGHG1,
PTRF,
PTGES3P1,
IGKV1.9,
ZNF607,
ENSG00000282458,
IGHGP,
RP13.270P17.3,
NRG1,
NUTM2B.AS1,
ENSG00000282416,
RP11.861A13.3,
RP11.81H14.2,
RP11.707023.5,
KIAA2018,
PM20D1, and
TREML4; or (ii) 5, 8, 10, or 12 or more of the genes:
LY6E,
IFIT1,
SIGLEC1,
RSAD2,
OASL,
GBP1,
ISG15,
IFIT5,
IFI27,
CCL2,
LAMP3,
DDX58,
ATF3, and
SEPT4;

(c) normalizing the gene product expression levels to generate normalized expression values;

(d) entering the normalized gene product expression values into a SARS-COV-2 (COVID-19) infection classifier, said classifier(s) comprising pre-defined weighting values for each of the gene products of the plurality of pre-determined gene products for the platform, optionally wherein said classifier is retrieved from one or more databases; and (e) calculating a presence or an etiology probability for the SARS-COV-2 (COVID-19) infection based upon said normalized expression values and said classifier, and optionally determining a threshold for the determination of SARS-COV-2 (COVID-19) infection, to thereby determine the presence or viral stage of SARS-COV-2 (COVID-19) infection in the subject, wherein the method further comprises administering to the subject determined to have a SARS-COV-2 (COVID-19) infection an antiviral therapy or an anti-SARS-COV-2 (COVID-19) therapy, wherein the antiviral therapy or anti-SARS-COV-2 (COVID-19) therapy comprises oseltamivir, remdesivir, an RNAi antiviral, inhaled ribavirin, a monoclonal antibody, a neuraminidase blocking agent, convalescent plasma, dexamethasone or an anticoagulation drug.

2. The method according to claim 1 in which the classifier comprises a classifier generated by a method comprising:

(a) obtaining biological samples from a plurality of subjects known to be suffering from COVID-19;

(b) measuring on said platform the expression levels of a plurality of pre-defined gene products in each of said biological samples, wherein the plurality of pre-defined gene products comprises:

(i) 10, 20, 30, 40, 50 or more of the genes:
AKT2,
LPCAT1,
CACNA1I,
HEATR5B,
PTMAP5,
TRAF6,
TMEM184B,
C15orf52,
PIF1,
NID1,
RPL36AL,
RHOB,
AOAH.IT1,
KLHDC8B,
RP11.925D8.3,
CETN2,
FAM13A.AS1,
PCGF3,
MDGA1,
IGHV1.24,
KEAP1,
CTD.2047H16.3,
HORMAD1,
PDHB,
MRAS,
PRRG4,
CTD.2357A8.2,
HNRNPA1P21,
CD70,
RP11.358B23.7,
BIRC5,
NKX3.1,
ZFHX3,
HOXA.AS2,
TBC1D19,
RP11.180M15.7,
IGHG1,
PTRF,
PTGES3P1,
IGKV1.9,
ZNF607,
ENSG00000282458,
IGHGP,
RP13.270P17.3,
NRG1,
NUTM2B.AS1,
ENSG00000282416,
RP11.861A13.3, RP11.81H14.2,
RP11.707023.5,
KIAA2018,
PM20D1, and
TREML4; or
(ii) 5, 8, 10, or 12 or more of the genes:
LY6E,
IFIT1,
SIGLEC1,
RSAD2,
OASL,
GBP1,
ISG15,
IFIT5,
IFI27,
CCL2,
LAMP3,
DDX58,
ATF3, and
SEPT4;

(c) normalizing the gene product expression levels obtained in step (b) to generate normalized expression values; and (d) generating a SARS-COV-2 (COVID-19) classifier for the platform based upon said normalized gene product expression values to thereby make the classifier for the platform, wherein the generating comprises, iteratively:

(i) assigning a weight for each of the normalized gene product expression values, entering the weight and expression value for each gene product into a classifier equation and determining a score for outcome for each of the plurality of subjects, then (ii) determining the accuracy of classification for each outcome across the plurality of subjects, and then (iii) adjusting the weight until accuracy of classification is optimized to provide said classifier for the platform, wherein analytes having a non-zero weight are included in the respective classifier.

3. The method according to claim 1 in which the method further comprises:

(f) entering the normalized gene product expression values into one or more additional classifier(s) selected from a non-COVID-19 viral infection classifier, a bacterial infection classifier, a non-infectious illness classifier, and a healthy subjects classifier, said classifier(s) comprising pre-defined weighted values for each of the gene products of the plurality of pre-determined gene products for the platform, optionally wherein said classifier(s) is retrieved from one or more databases; and (g) calculating a presence or an etiology probability for the one or more additional classifier(s) based upon said normalized expression values, and optionally determining a threshold for the determination of a non-COVID-19 viral infection, a bacterial infection, a non-infectious illness, and/or a healthy status in the subject.

4. The method according to claim 3 in which the additional classifier(s) comprise an influenza infection classifier, a non-COVID-19 coronavirus infection classifier, or a bacterial infection classifier.

5. The method according to claim 1, wherein the method comprises monitoring the subject's response to the antiviral therapy or anti-SARS-COV-2 (COVID-19) therapy.

* * * * *